(12) United States Patent
Wang

(10) Patent No.: US 12,685,472 B2
(45) Date of Patent: Jul. 21, 2026

(54) LIGHT-TRANSMITTING ELECTRODE STRUCTURE AND SMART WEARABLE DEVICE

(71) Applicant: GOERTEK INC., Shandong (CN)

(72) Inventor: Jianjun Wang, Shandong (CN)

(73) Assignee: GOERTEK INC., Shandong (CN)

( * ) Notice: Subject to any disclaimer, the term of this patent is extended or adjusted under 35 U.S.C. 154(b) by 298 days.

(21) Appl. No.: 18/553,207

(22) PCT Filed: Aug. 25, 2021

(86) PCT No.: PCT/CN2021/114445
§ 371 (c)(1),
(2) Date: Sep. 29, 2023

(87) PCT Pub. No.: WO2022/205751
PCT Pub. Date: Oct. 6, 2022

(65) Prior Publication Data
US 2024/0206791 A1 Jun. 27, 2024

(30) Foreign Application Priority Data
Mar. 29, 2021 (CN) .......................... 202110335878.0

(51) Int. Cl.
*A61B 5/28* (2021.01)
*A61B 5/256* (2021.01)
*H10H 20/833* (2025.01)

(52) U.S. Cl.
CPC ................ *A61B 5/28* (2021.01); *A61B 5/256* (2021.01); *H10H 20/833* (2025.01)

(58) Field of Classification Search
CPC ............ A61B 5/02427; A61B 5/02438; A61B 5/0245; A61B 5/681; H10H 20/833
See application file for complete search history.

(56) References Cited

U.S. PATENT DOCUMENTS

| | | |
|---|---|---|
| 10,729,347 B1 | 8/2020 | Schleicher |
| 2012/0071734 A1 | 3/2012 | Shimuta et al. |
| (Continued) | | |

FOREIGN PATENT DOCUMENTS

| | | |
|---|---|---|
| CN | 1723842 A | 1/2006 |
| CN | 102413761 A | 4/2012 |
| (Continued) | | |

*Primary Examiner* — Tammie K Marlen
(74) *Attorney, Agent, or Firm* — Ingrassia Fisher & Lorenz, LLP

(57) ABSTRACT

A light-transmitting electrode structure and an smart wearable device are disclosed. The light-transmitting electrode structure is installed on an outer surface of an electronic device, and comprises: a base, a transparent electrode layer, and a conductive connector. The transparent electrode layer covers an outer surface of the base. The conductive connector passes through the base to electrically connect the transparent electrode layer with an ECG circuit in the electronic device, so that the transparent electrode layer forms an ECG electrode. The base is provided with light-transmitting through holes which are aligned with an optical heart rate sensor in the electronic device, so that the transparent electrode layer forms a light-transmitting lens of the optical heart rate sensor.

12 Claims, 3 Drawing Sheets

(56)                    References Cited

U.S. PATENT DOCUMENTS

| | | | |
|---|---|---|---|
| 2015/0094552 A1* | 4/2015 | Golda ................... | A61B 5/282 |
| | | | 600/336 |
| 2016/0143554 A1 | 5/2016 | Lin et al. | |
| 2018/0220972 A1 | 8/2018 | Jeong et al. | |
| 2019/0069848 A1 | 3/2019 | Clavelle et al. | |
| 2020/0029834 A1 | 1/2020 | Tang et al. | |

FOREIGN PATENT DOCUMENTS

| | | |
|---|---|---|
| CN | 104055499 A | 9/2014 |
| CN | 105233404 A | 1/2016 |
| CN | 206877213 U | 1/2018 |
| CN | 108388308 A | 8/2018 |
| CN | 109363649 A | 2/2019 |
| CN | 210666389 U | 6/2020 |
| CN | 210669548 U | 6/2020 |
| CN | 112043055 A | 12/2020 |
| CN | 212118134 U | 12/2020 |
| CN | 113171099 A | 7/2021 |

* cited by examiner

LIGHT-TRANSMITTING ELECTRODE STRUCTURE AND SMART WEARABLE DEVICE

CROSS-REFERENCE TO RELATED APPLICATIONS

This Application is a U.S. National-Stage entry under 35 U.S.C. § 371 based on International Application No. PCT/CN2021/114445, filed Aug. 25, 2021 which was published under PCT Article 21(2) and which claims priority to Chinese Application No. 202110335878.0, filed Mar. 29, 2021, which are all hereby incorporated herein in their entirety by reference.

TECHNICAL FIELD

This application pertains to the technical field of wearable devices, in particular to a light-transmitting electrode structure and an smart wearable device.

BACKGROUND

With people's increasing awareness of health, health devices have become more and more diverse. Among them, wearable smart health devices, due to their convenience, are very practical for ordinary users to check their physical health, and thus are favored by the market. Wearable smart health devices can measure electrocardiogram (ECG), heart rate, blood pressure, etc. The electrocardiogram measurement needs an electrode in contact with the human body. The heart rate is usually measured by optical measurement methods.

However, in conventional wearable devices, the electrode device for human ECG measurement and the optical lens device for heart rate measurement occupy too much space, resulting in the wearable devices being too large and inconvenient to design. In addition, most ECG electrodes are made entirely of metal material and thus are relatively expensive. In addition, other objects, desirable features and characteristics will become apparent from the subsequent summary and detailed description, and the appended claims, taken in conjunction with the accompanying drawings and this background.

SUMMARY

In view of the problems in the conventional wearable devices that the ECG measurement device and the heart rate measurement device occupy too much space and the design is poor, the present disclosure proposes a light-transmitting electrode structure and a smart wearable device to overcome the above problems.

In order to achieve the above object, the following technical solutions are adopted in the present disclosure.

According to an aspect of the present disclosure, a light-transmitting electrode structure is provided. The light-transmitting electrode structure is installed on an outer surface of an electronic device and comprises: a base, a transparent electrode layer, and a conductive connector;

wherein the transparent electrode layer covers an outer surface of the base;

the conductive connector passes through the base to electrically connect the transparent electrode layer with an ECG circuit in the electronic device, so that the transparent electrode layer forms an ECG electrode; and the base is provided with light-transmitting through holes which are aligned with an optical heart rate sensor in the electronic device, so that the transparent electrode layer forms a light-transmitting lens of the optical heart rate sensor.

Optionally, the transparent electrode layer is a non-metallic conductive film, and covers the outer surface of the base by an in-mold labeling process.

Optionally, colored conductive ink is printed between the base and the transparent electrode layer except in regions of the light-transmitting through holes.

Optionally, the transparent electrode layer comprises an integral piece or multiple pieces spliced together, and the multiple pieces of the transparent electrode layers are insulatedly separated by blocking ribs, and each piece of the transparent electrode layer is connected to an independent conductive connector respectively.

Optionally, the base is provided with a through hole for electrical connection, the conductive connector is conductive foam, and the conductive foam passes through the through hole for electrical connection to electrically connect the transparent electrode layer with the ECG circuit in the electronic device;

or, the base is provided with a through groove, the conductive connector is elastic conductive adhesive, and the elastic conductive adhesive is poured into the through groove to electrically connect the transparent electrode layer with the ECG circuit in the electronic device.

Optionally, the base is provided with charging pins which are connected to a charging circuit in the electronic device, and the transparent electrode layer is provided with charging holes for exposing the charging pins.

Optionally, the base is made of a plastic material.

According to another aspect of the present disclosure, a smart wearable device is provided. The smart wearable device comprises an ECG circuit and an optical heart rate sensor. The casing of the smart wearable device comprises the light-transmitting electrode structure as described in the above items.

Optionally, the smart wearable device is a smartwatch, and the light-transmitting electrode structure is disposed on a side of the smartwatch that contacts the wrist.

Optionally, the light-transmitting electrode structure is sealedly and adhesively bonded to the smart wearable device by a waterproof adhesive.

In sum, the beneficial effects of the present disclosure are as follows.

The light-transmitting electrode structure of the present disclosure integrates two functions: the ECG electrode and the heart rate light-transmitting lens. It can not only detect electrical signals on the human body surface for ECG measurement, but also enable optical heart rate sensors to emit and receive light, thereby integrating ECG measurement and heart rate measurement into the same electrode structure and thus saving space.

In addition, in a preferred embodiment of the present disclosure, the transparent electrode layer is a non-metallic conductive film, and the base is a plastic base. They replaced the metal electrode in the prior art, the use of metal materials can be reduced, and thus the cost of electrode can be reduced.

BRIEF DESCRIPTION OF DRAWINGS

The present invention will hereinafter be described in conjunction with the following drawing figures, wherein like numerals denote like elements, and.

Figure 1:
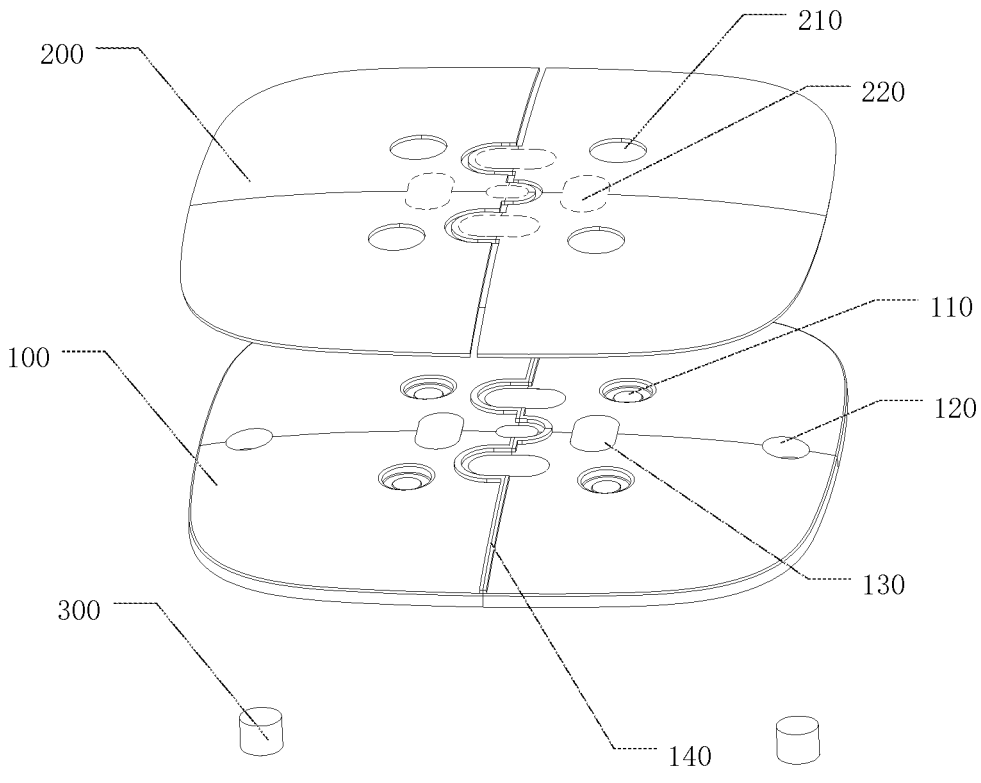
FIG. 1 is a schematic exploded view of a light-transmitting electrode structure according to an embodiment of the present disclosure.

In the drawings: 100, base; 110, charging pin; 120, through hole for electrical connection; 130, light-transmitting through hole; 140, blocking rib; 200, transparent electrode layer; 210, charging hole; 220), non-ink printing region; 300, conductive connector.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

In order to make the objectives, technical solutions, and advantages of the present application clearer, the embodiments of the present disclosure will be further described in details in conjunction with the drawings.

In the description of the present disclosure, it should be noted that orientation or positional relationship indicated by the terms "center", "upper", "lower", "left", "right", "vertical", "horizontal", "inside", "outside", etc. are orientation or positional relationship based on the drawings, which are merely for convenience of describing the present disclosure and simplifying the description, rather than indicating or implying that the device or element referred to must have a specific orientation, or must be constructed and operated with a specific orientation, they should not be construed as limiting the present disclosure. In addition, the terms "first," "second," and "third" are merely for convenience of describing the present disclosure and cannot be understood as indicating or implying relative importance.

In the description of the present disclosure, it should be noted that unless otherwise expressly specified and defined, the terms "installed", "connected" and "fixed" should be understood in a broad sense, for example, it may be fixedly connected, or removably connected, or integrally connected; it may also be mechanically connected or electrically connected; it may also be directly connected or indirectly connected through a middleware; it may also be internally communicated or interacted between two components. For a person of ordinary skill in the art, the specific meaning of these terms in the present disclosure should be understood according to specific situations.

The technical concept of the present disclosure is that, the light-transmitting electrode structure of the present disclosure integrates two functions: the ECG electrode and the heart rate light-transmitting lens. It can not only detect electrical signals on the human body surface for ECG measurement, but also enable optical heart rate sensors to emit and receive light, thereby integrating ECG measurement and heart rate measurement into the same electrode structure and thus saving space.

FIGS. 1 to 5 illustrate an embodiment of the schematic structure of the light-transmitting electrode of the present disclosure.

As shown in FIGS. 1 to 5, the light-transmitting electrode structure of the present disclosure is used for installation on an outer surface of an electronic device. It comprises a base 100, a transparent electrode layer 200, and a conductive connector 300. The transparent electrode layer 200 covers an outer surface of the base 100. The conductive connector 300 passes through the base 100 and electrically connects the transparent electrode layer 200 with an ECG circuit in the electronic device, so that the transparent electrode layer 200 forms an ECG electrode. Moreover, the base 100 is provided with several light-transmitting through holes 130 which are aligned with an optical heart rate sensor in the electronic device, so that the transparent electrode layer 200 forms a light-transmitting lens of the optical heart rate sensor.

Thus, in the light-transmitting electrode structure of this embodiment, the transparent electrode layer 200 provided on the base 100 can conduct electricity and is connected to the ECG circuit in the electronic device via the conductive connector 300, thereby achieving the function of ECG measurement. At the same time, the transparent electrode layer 200 can cooperate with the light-transmitting through holes 130 on the base 100 to enable the light for heart rate measurement to pass through without obstacles, thereby achieving the function of heart rate measurement. Therefore, this embodiment integrates the function of ECG electrodes and the function of light-transmitting lenses for heart rate measurement, thereby effectively reducing the volume of the health measurement device, which is conducive to the miniaturization and lightweight design of wearable health devices.

In an embodiment of the present disclosure, the transparent electrode layer 200 is a non-metallic conductive film, and covers the outer surface of the base 100 by an in-mold labeling process. In-mold labeling (IML) process is a new technology that places a thin film inside an injection mold to decorate the appearance of plastic. It is characterized in that the surface of the molded structure is a layer of light-transmitting film, with a printed pattern layer in the middle and a plastic layer on the back. Since the pattern layer is located inside, it is not easy to wear and fade, and thus the molded structure is more durable.

In an embodiment of the present disclosure, colored conductive ink is printed between the base 100 and the transparent electrode layer 200 except in regions of the light-transmitting through holes 130. Colored conductive ink can mask the internal structure of electronic devices, thereby avoiding adverse effects on the appearance caused by seeing the internal structure of electronic devices through the transparent electrode layer 200.

Figure 2:
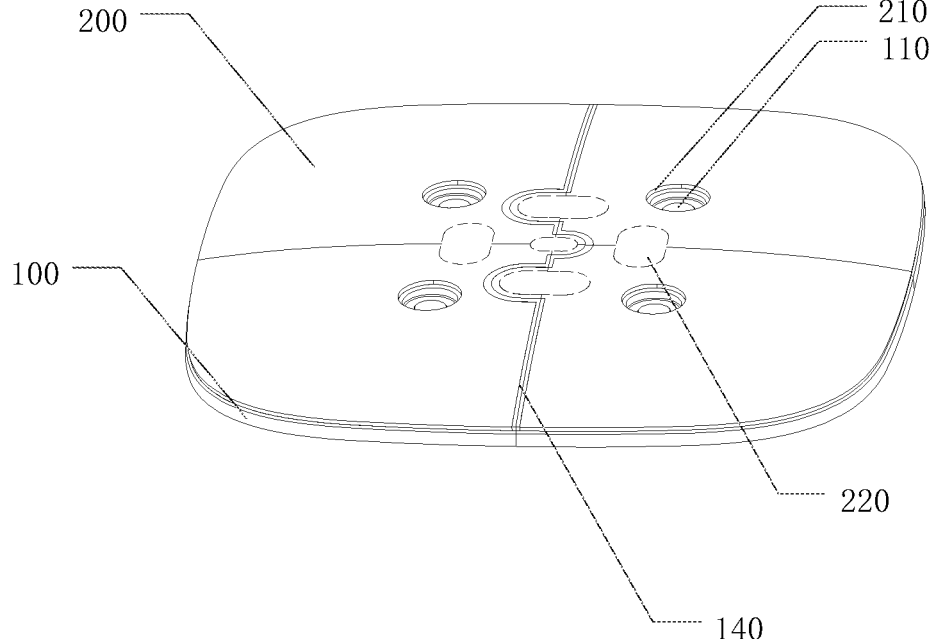
FIG. 2 is a schematic front view of a light-transmitting electrode structure according to an embodiment of the present disclosure.

As shown in FIGS. 1 to 2, the regions with dashed lines on the transparent electrode layer 200 are non-ink printing regions 220, which are aligned with the light-transmitting through holes 130. The non-ink printing regions 220 are not provided with colored conductive ink so as to ensure the smooth transmission of light for heart rate measurement. In this embodiment, since the IML process is used and the colored conductive ink is sandwiched between the transparent electrode layer 200 and the base 100, the colored conductive ink can be effectively prevented from being scratched, the friction resistance can be improved, the bright color of the colored conductive ink can maintain for a long time and is not easy to fade, and thus the appearance design level of electronic devices can be improved.

In an embodiment of the present disclosure, the transparent electrode layer 200 comprises an integral piece or multiple pieces spliced together, thereby forming one or more ECG electrodes. When the transparent electrode layers 200 spliced by multiple pieces is used, as shown in FIGS. 1 to 5, the multiple pieces of the transparent electrode layer 200 are insulatedly separated by blocking ribs 140, and each piece of the transparent electrode layer 200 is connected to an independent conductive connector 300 respectively. In the embodiment shown in FIGS. 1 to 5, the transparent electrode layer 200 comprises two pieces spliced together, which form two ECG electrodes through two independent conductive connectors 300.

Figure 3:
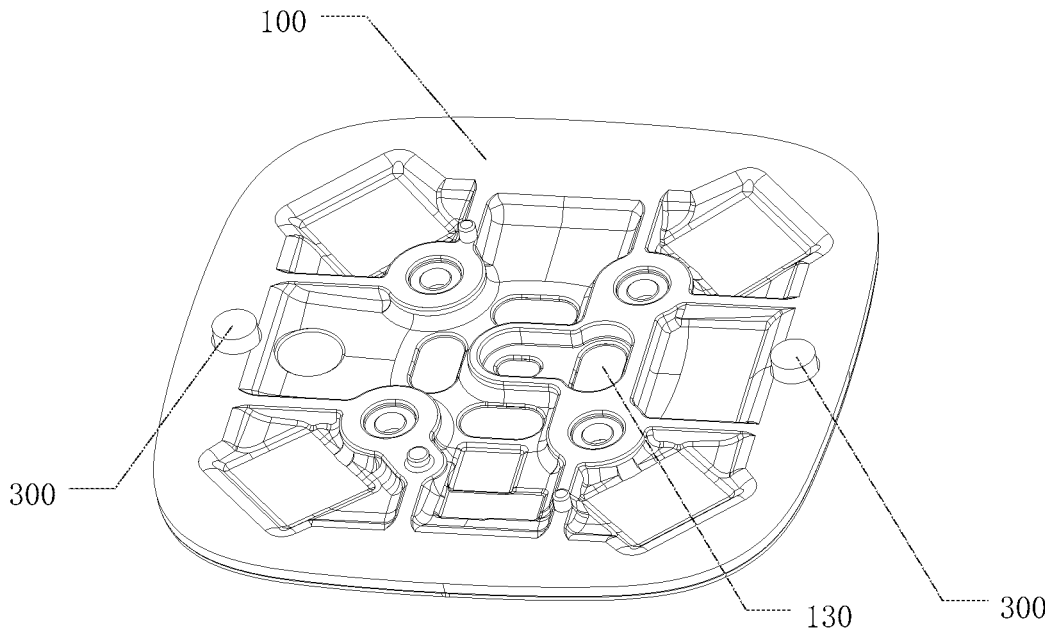
FIG. 3 is a schematic rear view of a light-transmitting electrode structure according to an embodiment of the present disclosure.

In an embodiment of the present disclosure, as shown in FIGS. 2 to 3, the base 100 is provided with a through hole 120 for electrical connection, the conductive connector 300 is made of conductive foam, and the conductive foam passes through the through hole 120 for electrical connection to electrically connect the transparent electrode layer 200 with the ECG circuit in the electronic device.

Alternatively, in some other embodiments of the present disclosure, the base 100 is provided with a through groove, the conductive connector 300 is elastic conductive adhesive, and the elastic conductive adhesive is poured into the through groove to electrically connect the transparent electrode layer 200 with the ECG circuit in the electronic device.

Figure 4:
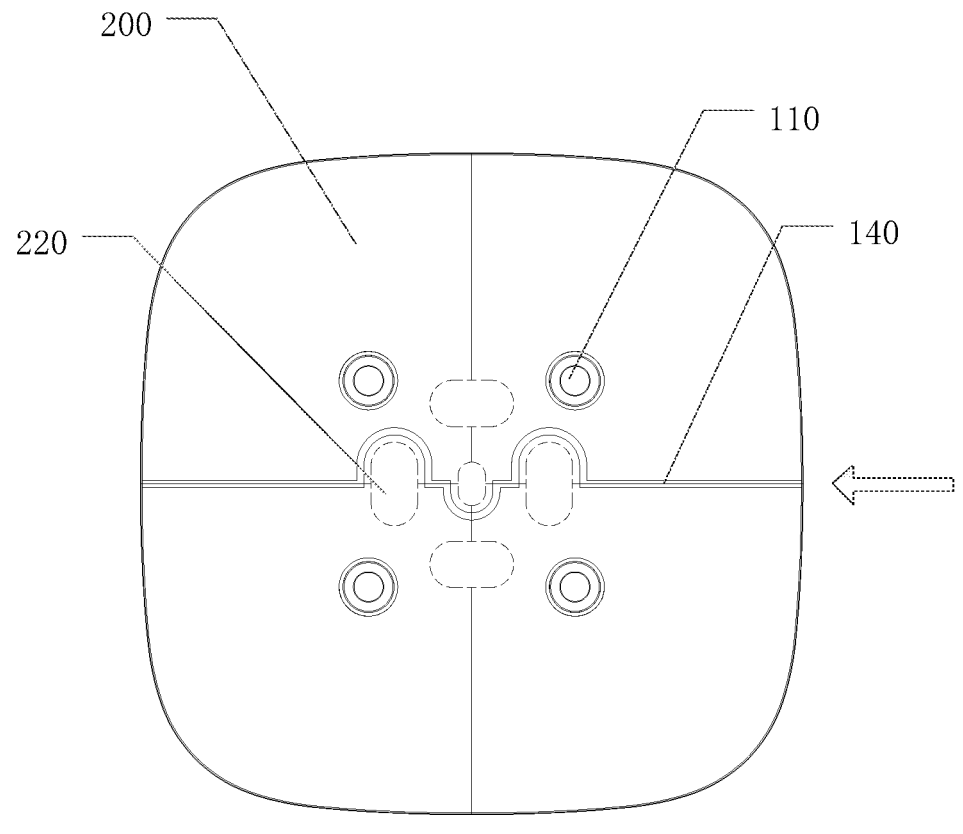
FIG. 4 is a schematic top view of a light-transmitting electrode structure according to an embodiment of the present disclosure.
Figure 5:
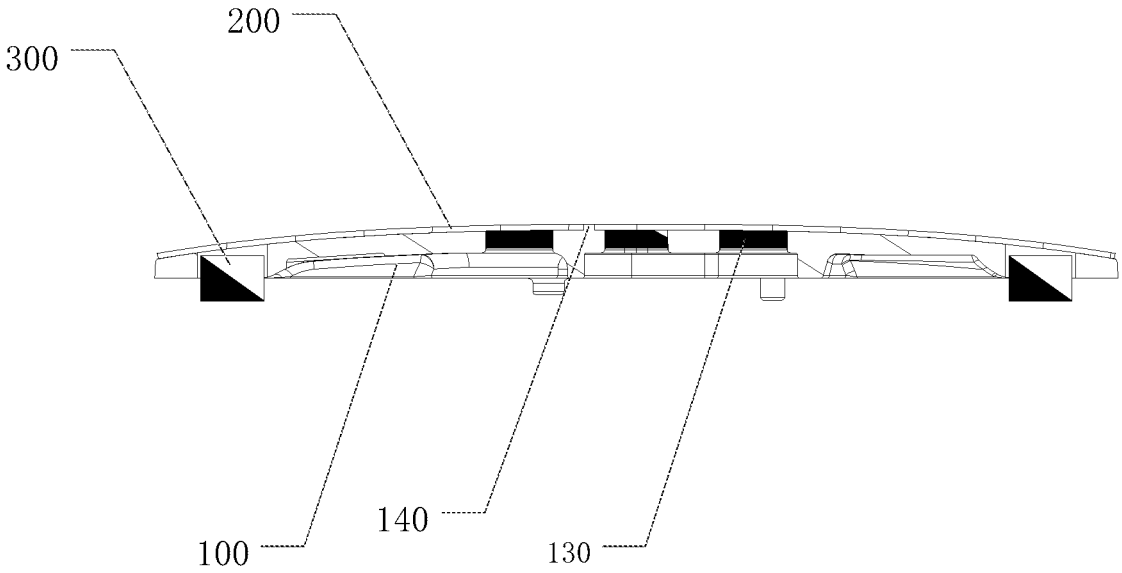
FIG. 5 is a schematic cross-sectional view of a light-transmitting electrode structure according to an embodiment of the present disclosure, viewed in the direction of the arrow shown in FIG. 4.

In an embodiment of the present disclosure, as shown in FIGS. 1, 2, and 4. the base 100 is provided thereon with several charging pins 110, which are connected to a charging circuit in the electronic device. The transparent electrode layer 200 is provided with charging holes 210 for exposing the charging pins 110 to achieve contact charging of the electronic device. Thus, in this embodiment of the light-transmitting electrode structure of the present disclosure, the charging module is further integrated, and the spatial utilization rate of the light-transmitting electrode structure can be more effectively improved.

In an embodiment of the present disclosure, the base 100 is made of plastic material. The blocking ribs 140 are a part of the base 100 and are integrally formed by injection molding or other methods. In this embodiment, the plastic base 100 and the non-metallic transparent electrode layer 200 are used to replace the metal electrode in the conventional design, so the use of metal materials can be reduced, which not only reduces the weight of electronic devices, but also helps to reduce product costs.

The present disclosure also discloses a smart wearable device. In an embodiment of the present disclosure, the smart wearable device comprises an ECG circuit and an optical heart rate sensor, and the casing of the smart wearable device comprises the light-transmitting electrode structure as described in any of the above items. Thus, the smart wearable device according to this embodiment can achieve both ECG testing and heart rate testing by the above light-transmitting electrode structure, and even achieve contact charging, and thus can be more lightweight and miniaturized.

In an embodiment of the present disclosure, the smart wearable device is a smart watch, and the light-transmitting electrode structure is disposed on a side of the smartwatch that contacts the wrist.

In an embodiment of the present disclosure, the light-transmitting electrode structure is sealedly and adhesively bonded to the smart wearable device by a waterproof adhesive, thereby achieving waterproofing and dust prevention of the smart wearable device.

In an embodiment of the present disclosure, the optical heart rate sensor of the smart wearable device comprises one or more light emitting diodes. The light-transmitting through holes 130 on the light-transmitting electrode structure are arranged according to the structure of the optical heart rate sensor. In the embodiment shown in FIGS. 1 to 5 of the present disclosure, there are five light-transmitting through holes 130. In other embodiments of the present disclosure, the light-transmitting through holes 130 may be set to other quantities and arrangements, which will not be described in detail here.

In sum, the light-transmitting electrode structure of the present disclosure integrates two functions: the ECG electrode and the heart rate light-transmitting lens. It can not only detect electrical signals on the human body surface for ECG measurement, but also enable optical heart rate sensors to emit and receive light, thereby integrating ECG measurement and heart rate measurement into the same electrode structure and thus saving space. In addition, in a preferred embodiment of the present disclosure, the transparent electrode layer is a non-metallic conductive film, and the base is a plastic base. If they replace the metal electrode in the prior art, the use of metal materials can be reduced, and thus the cost of electrode can be reduced.

The above merely describes particular embodiments of the present disclosure. By the teaching of the present disclosure, a person skilled in the art can make other modifications or variations based on the above embodiments. A person skilled in the art should appreciate that, the detailed description above is only for the purpose of explaining the present disclosure, and the protection scope of the present disclosure should be subject to the protection scope of the claims.

The following detailed description is merely exemplary in nature and is not intended to limit the invention or the application and uses of the invention. Furthermore, there is no intention to be bound by any theory presented in the preceding background of the invention or the following detailed description.

What is claimed is:

1. A light-transmitting electrode structure installed on an outer surface of an electronic device, comprising: a base, a transparent electrode layer, and a conductive connector;

wherein the transparent electrode layer covers an outer surface of the base;

the conductive connector passes through the base to electrically connect the transparent electrode layer with an ECG circuit in the electronic device, so that the transparent electrode layer forms an ECG electrode; and the base is provided with light-transmitting through holes which are aligned with an optical heart rate sensor in the electronic device, so that the transparent electrode layer forms a light-transmitting lens of the optical heart rate sensor, wherein the transparent electrode layer is a non-metallic conductive film, and covers the outer surface of the base by an in-mold labeling process, and wherein a colored conductive ink is printed between the base and the transparent electrode layer except in regions of the light-transmitting through holes, the transparent electrode layer provided on the base conducts electricity and is connected to the ECG circuit in the electronic device via the conductive connector to achieve the function of ECG measurement, at the same time, the transparent electrode layer cooperates with the light-transmitting through holes on the base to enable the light for heart rate measurement to pass through without obstacles, and achieves the function of heart rate measurement, wherein the transparent electrode layer comprises multiple pieces spliced together, and the multiple pieces of the transparent electrode layers are insulatedly separated by blocking ribs, and each piece of the transparent electrode layer is connected to an independent conductive connector respectively, the blocking ribs are integrally formed with the base by injection molding.

2. The light-transmitting electrode structure according to claim 1, wherein the base is provided with a through hole for electrical connection, the conductive connector is conductive foam, and the conductive foam passes through the through hole for electrical connection to electrically connect the transparent electrode layer with the ECG circuit in the electronic device;

or, the base is provided with a through groove, the conductive connector is elastic conductive adhesive, and the elastic conductive adhesive is poured into the through groove to electrically connect the transparent electrode layer with the ECG circuit in the electronic device.

3. The light-transmitting electrode structure according to claim 1, wherein the base is provided with charging pins which are connected to a charging circuit in the electronic device, and the transparent electrode layer is provided with charging holes for exposing the charging pins.

4. The light-transmitting electrode structure according to claim 1, wherein the base is made of a plastic material.

5. A smart wearable device, comprising an ECG circuit and an optical heart rate sensor, a casing of the smart wearable device comprises a light-transmitting electrode structure, wherein the light-transmitting electrode structure installed on an outer surface of the smart wearable device, and comprises: a base, a transparent electrode layer, and a conductive connector;

the transparent electrode layer covers an outer surface of the base;

the conductive connector passes through the base to electrically connect the transparent electrode layer with an ECG circuit in the electronic device, so that the transparent electrode layer forms an ECG electrode; and the base is provided with light-transmitting through holes which are aligned with an optical heart rate sensor in the electronic device, so that the transparent electrode layer forms a light-transmitting lens of the optical heart rate sensor, the transparent electrode layer is a non-metallic conductive film, and covers the outer surface of the base by an in-mold labeling process, a colored conductive ink is printed between the base and the transparent electrode layer except in regions of the light-transmitting through holes, the transparent electrode layer provided on the base conducts electricity and is connected to the ECG circuit in the electronic device via the conductive connector to achieve the function of ECG measurement, at the same time, the transparent electrode layer cooperates with the light-transmitting through holes on the base to enable the light for heart rate measurement to pass through without obstacles, and achieves the function of heart rate measurement, wherein the transparent electrode layer comprises multiple pieces spliced together, and the multiple pieces of the transparent electrode layers are insulatedly separated by blocking ribs, and each piece of the transparent electrode layer is connected to an independent conductive connector respectively, the blocking ribs are integrally formed with the base by injection molding.

6. The smart wearable device according to claim 5, wherein the smart wearable device is a smartwatch, and the light-transmitting electrode structure is disposed on a side of the smartwatch that contacts the wrist.

7. The smart wearable device according to claim 5, wherein the light-transmitting electrode structure is sealedly and adhesively bonded to the smart wearable device by a waterproof adhesive.

8. The smart wearable device according to claim 5, wherein the transparent electrode layer comprises an integral piece or multiple pieces spliced together, and the multiple pieces of the transparent electrode layers are insulatedly separated by blocking ribs, and each piece of the transparent electrode layer is connected to an independent conductive connector respectively.

9. The smart wearable device according to claim 5, wherein the base is provided with a through hole for electrical connection, the conductive connector is conductive foam, and the conductive foam passes through the through hole for electrical connection to electrically connect the transparent electrode layer with the ECG circuit in the electronic device;

or, the base is provided with a through groove, the conductive connector is elastic conductive adhesive, and the elastic conductive adhesive is poured into the through groove to electrically connect the transparent electrode layer with the ECG circuit in the electronic device.

10. The smart wearable device according to claim 5, wherein the base is provided with charging pins which are connected to a charging circuit in the electronic device, and the transparent electrode layer is provided with charging holes for exposing the charging pins.

11. The smart wearable device according to claim 5, wherein the base is made of a plastic material.

12. The smart wearable device according to claim 8, wherein the base is provided with a through hole for electrical connection, the conductive connector is conductive foam, and the conductive foam passes through the through hole for electrical connection to electrically connect the transparent electrode layer with the ECG circuit in the electronic device;

or, the base is provided with a through groove, the conductive connector is elastic conductive adhesive, and the elastic conductive adhesive is poured into the through groove to electrically connect the transparent electrode layer with the ECG circuit in the electronic device.

* * * * *